United States Patent [19]

Noll et al.

[11] Patent Number: 5,370,876

[45] Date of Patent: Dec. 6, 1994

[54] ANTIMICROBIAL PROTECTIVE SKIN COMPOSITION AND METHOD FOR PROTECTING SKIN FROM BODY FLUIDS

[75] Inventors: Charles R. Noll; Virginia M. Noll, both of Pulaski, Wis.

[73] Assignee: Microbarriers, Pulaski, Wis.

[21] Appl. No.: 1,837

[22] Filed: Jan. 8, 1993

[51] Int. Cl.$^5$ ............... A01N 25/24; A61L 15/00
[52] U.S. Cl. ................. 424/407; 424/445; 514/50; 514/157; 514/718; 514/938
[58] Field of Search ............... 424/407, 445; 514/938, 514/50, 718, 157

[56] References Cited

U.S. PATENT DOCUMENTS

| | | | |
|---|---|---|---|
| 2,698,824 | 1/1955 | Morgulis | 167/90 |
| 3,890,264 | 6/1975 | Sidi et al. | 260/29.6 HN |
| 3,929,705 | 12/1975 | Minieri | 260/29.6 HN |
| 3,952,000 | 4/1976 | Sidi et al. | 260/307 FA |
| 3,962,271 | 6/1976 | Sidi et al. | 260/307 FA |
| 4,012,261 | 3/1977 | Sidi et al. | 106/15 R |
| 4,022,906 | 5/1977 | Sidi et al. | 424/272 |
| 4,343,788 | 8/1982 | Mustacich | 424/78 |
| 4,404,196 | 9/1983 | Dandt et al. | 424/184 |
| 4,448,906 | 5/1984 | Deinet et al. | 523/122 |
| 4,467,013 | 8/1984 | Baldwin | 428/289 |
| 4,479,795 | 10/1984 | Mustacich | 604/53 |
| 4,500,338 | 2/1985 | Young et al. | 71/67 |
| 4,614,675 | 9/1986 | Ona et al. | 424/387 |
| 4,671,957 | 6/1987 | Holtshousen | 424/80 |
| 4,738,987 | 4/1988 | Mattson et al. | 514/770 |
| 4,803,066 | 2/1989 | Edwards | 424/132 |
| 5,019,604 | 5/1991 | Lemole | 523/105 |
| 5,039,711 | 8/1991 | Blount | 521/105 |
| 5,043,155 | 8/1991 | Puchalski et al. | 424/78 |
| 5,126,136 | 6/1992 | Merat et al. | 424/401 |
| 5,194,172 | 3/1993 | Taneri et al. | 252/130 |

FOREIGN PATENT DOCUMENTS

WO92/17184 10/1992 WIPO.

OTHER PUBLICATIONS

S. Budavari et al., The Merck Index (11th Ed.), 1989, pp. 51, 168, 715, 1055, 1151 and 1597.

Hoover et al., Remington's Pharmaceutical Sciences (15th Ed.), 1975, pp. 1224 and 1644–45.

Yamamoto et al., Chemical Abstracts, Oil-in-Water Solid Cosmetic Emulsions, vol. 116, No. 8, Abstract No. 66921w, JP03141211 (1991).

David H. Blount, Chemical Abstracts, Polyol-Alkali Metal Silicate Emulsion, vol. 98, No. 26, Abstract No. 216607z, US, A, 4,376,178 (1983).

*Primary Examiner*—Marianne M. Cintins
*Assistant Examiner*—Minna Moezie
*Attorney, Agent, or Firm*—Birch, Stewart, Kolasch & Birch

[57] ABSTRACT

A protective cream composition contains 15 to 40 wt. % of an alkali metal fatty acid salt having from 8 to 18 carbon atoms, an effective amount an antimicrobial compound, 5 to 20 wt. % of a polyol effective as an emollient, 0.5 to 8.0 wt. %, of an alkali metal silicate, and the balance water. Such a composition can be applied to the skin to protect health care workers and others from infection. The cream dries to form a topical barrier on the skin, and also contains an agent effective against, for instance, viruses such as human HIV. Once a medical operation is completed, the film formed from the dried cream can be washed off with soap and water.

16 Claims, No Drawings

ANTIMICROBIAL PROTECTIVE SKIN COMPOSITION AND METHOD FOR PROTECTING SKIN FROM BODY FLUIDS

FIELD OF THE INVENTION

This invention relates to a protective composition, more particularly to a skin cream of the kind that forms a protective film on skin or other surfaces.

BACKGROUND OF THE INVENTION

Many known antimicrobial topical compositions are designed for treatment of existing wounds or skin disorders, and are not used as barriers to future infectious contact. These topical agents penetrate the wound or infected area, and deliver the antimicrobial compound to the site of the contamination. Many of these commercially available topical formulations consist of an oil based carrier such as petrolatum or liquid paraffin which is insoluble or nearly insoluble in water, plus a bioactive agent. Such compositions tend to be greasy, tacky, stain causing, and may be difficult to remove. Specific topical bioactive skin ointments used to treat infections are described, for example, in Edwards U.S. Pat. No. 4,803,066, issued Feb. 7, 1989, and Holtshousen U.S. Pat. No. 4,671,957, issued Jun. 9, 1987.

Other antimicrobial surface-coating compositions have been formulated for the coating of substrates such as wood, metal, textile, thread, canvas, carpeting, paper and masonry. Most of these compounds are long lasting, toxic, irritating to skin, and not easily removable. Many are formulated to provide a semipermanent polymer coating. Ona et al. U.S. Pat. No. 4,614,675, issued Sep. 30, 1986, and Baldwin U.S. Pat. No. 4,467,013, issued Aug. 21, 1984, describe an antimicrobic used to treat fibers, fiber-containing material and non-woven fabrics. Mustacich et al. U.S. Pat. Nos. 4,479,795 and 4,343,788 describe a carboxylate antimicrobial agent releasably incorporated into permeable polymers. Young et al. U.S. Pat. No. 4,500,338, issued Feb. 19, 1985, discloses a hydrolyzable organic titanium compound containing a microbiocide and an optional organopolysiloxane for use as a surface disinfectant.

Other prior art has focused on the incorporation of an antimicrobial agent into surface coating substances such as paints or varnishes to prevent the decomposition of the surface coating. Deinet et al. U.S. Pat. No. 4,448,906, issued May 15, 1984, Dandt et al. U.S. Pat. No. 4,404,196, issued Sep. 13, 1983, Sidi et al. U.S. Pat. Nos. 4,022,906, issued May 10, 1977, 4,012,261, issued Mar. 15, 1977, 3,962,271, issued Jun. 8, 1976, 3,952,000, issued Apr. 20, 1976, 3,890,264, issued Jun. 17, 1975, and Minieri U.S. Pat. No. 3,929,705, issued Dec. 30, 1975 all describe such inventions.

In the field of protective hand creams, one composition marketed under the Invisible Glove trademark is made of about 60% water, 14% glycerin, 1% sodium silicate, and 25% soap (sodium laurate). This composition has been commercially successful as a cream applied prior to undertaking a task that involves exposing the hands to inks, grease, paints or the like. The cream dries to form a thin, slightly tacky film on the hands that repels contaminants. Mattson et al. U.S. Pat. No. 4,738,987 discloses a comparable skin care composition compounded as a dispersion of water with soap, a water-soluble alkali metal silicate, and sulfonated castor oil having a pH adjusted with acid to 6.5 to 10. See also Morgulis U.S. Pat. No. 2,698,824, issued Jan. 4, 1955, which describes a non-bioactive silicone-based ointment which provides a non water soluble protective layer on the skin.

These compositions tend to fall into one of several categories: compositions containing an antimicrobial designed for immediate use on the skin, compositions containing an antimicrobial and an agent such as a siloxane to provide extended substantivity on the skin, and compositions for temporary use (i.e., which wash off readily with soap and water) but which lack an antimicrobial. None are particularly suited for protecting health care workers. During surgery, doctors and health care workers are commonly exposed to the blood or other bodily fluids of the patient. Protective gowns, masks and gloves may not provide adequate protection of all exposed skin areas, and may hinder delicate operations. A need exists for a skin protectant composition that can be worn under of protective clothing and on skin which remains exposed, which composition minimizes the chance that a health care worker will contract AIDS or other infectious diseases. However, the composition should be readily removable when a procedure or operation is over so that the physician or health care worker can wash it off and remove any residual contamination. The present invention addresses this need.

SUMMARY OF THE INVENTION

This invention provides a protective composition, particularly a skin cream, from formulations of an aqueous base, preferably an oil-in-water emulsion, containing an antimicrobial agent. A preferred antimicrobial protective composition according to the invention contains, as basic ingredients, an alkali-metal fatty acid salt, an antimicrobial agent, an alkali-metal silicate, and water. In particular, a preferred skin cream which provides a barrier from viruses, bacteria and other microorganisms consists essentially of 15 to 40 wt. % of an alkali metal fatty acid salt having from 8 to 18 carbon atoms, an effective amount, generally about 0.1 to 15.0 wt. %, of an antimicrobial compound, 0.5 to 8.0 wt. % of an alkali-metal silicate, up to 20 wt. % of a polyol effective as an emollient and/or viscosity adjusting agent, and the balance water. In each case, weight percent amounts are based on the weight of the total composition. Such a composition dries quickly on the skin and forms a film that repels liquids and also kills "germs" that might otherwise survive to eventually penetrate the barrier.

According to a further aspect of the invention, the foregoing composition is used in carrying out one or a series of surgeries or medical procedures. The subject applies the cream according to the invention to his or her skin in likely exposed areas, such as hands, face and upper body, puts on protective clothing, and performs the operation or procedure. After the operation is over, for example, the subject washes the film left by the cream off. If a further operation is scheduled, the cream can then be freshly reapplied without danger of residual contamination from the prior operation. These and other aspects of the invention are more fully described below.

DETAILED DESCRIPTION OF THE INVENTION

As discussed above, a need exists for a topical barrier containing a microbiocide that provides protection by direct application to exposed skin and may be easily removed with water. A composition for administration to the skin to form an adherent, continuous, flexible coat should serve two purposes: (1) it should form a barrier against infection, and (2) it should serve as an effective vehicle for one or more antimicrobial agents that destroy infectious organisms that come in contact with the topical barrier. Such a composition could be used in place of gloves in some circumstances, or may be used to provide an extra measure of protection underneath gloves or on areas the gloves do not cover, such as the forearms, and would be of immense use to individuals such as health care workers, police, fire and rescue personnel, and anyone else who is at risk of exposure to infectious bodily fluids.

Ideally, a skin cream should be non-toxic, without side effects, non-irritating, non-greasy, non-tacky, odorless, easy to apply, easy to remove, and provide excellent protection from infection. It should provide an effective barrier for an extended time (for example, up to 4 hours, preferably up to 24 hours) or until removed. The present invention can provide these characteristics to a greater extent than many prior preparations.

Any compatible antimicrobial agent of the kind presently employed in cream/ointment formulations may be used in the topical antimicrobial composition of the invention. Suitable agents may possess antiviral, antibacterial and other activities. Preferred antimicrobial agents include those which have been shown to be effective against the HIV virus such as Nonoxynol-9 (nonylphenoxypolyethoxyethanol) and AZT (azidothymidine, or zidovudine). Other useful antimicrobials include chlorhexidene, iodine, sodium oxychlorosene, tetrachlorosalicylanilide, silver sulfadiazine, butaconazole nitrate, chloroxylenol, and fungicidal agents such as triacetin and aluminum chlorhydrate. A preferred antimicrobial agent for this invention is Nonoxynol-9, because this agent has proven safe and effective for human use.

The concentration of antimicrobial/biocidal agent in the present invention will depend on the antimicrobial strength required. Usually only a small amount of the antimicrobial compound is needed. The addition of as little as 0.1% by weight of one or more of the antimicrobial agent will usually provide a measurable increase in protection. A range of 0.1 to 15 wt. % is preferred because excess amounts of the antimicrobial compound ordinarily do not provide further improvement in the properties of the surface-coating compositions and reduce the effectiveness of the skin barrier.

The precise amount of antimicrobial compound that will provide optimum protection for a given composition will depend on such factors as the activity of the particular antimicrobial compound employed, its toxicity, the propensity of the compound to cause irritation, the duration of use contemplated, the choice of materials which make up the cream base, and the application for which the coating compound is intended. Accordingly, the amount of the antimicrobial agent may vary widely, and combinations of several agents having different activities may be desirable.

The antimicrobial agent is preferably dispersed in an oil-in-water (o/w) emulsion base comprised of an alkali metal fatty acid salt such as sodium palmitate or sodium laurate, an alkali-metal silicate such as sodium or potassium silicate, in water. The water soluble salts of fatty acids, derived from alkaline hydrolysis (saponification) of plant or animal fats and oils which are widely used in cosmetic products, are used in the invention to provide water-repellency.

Alkali-metal salts of saturated or unsaturated fatty acids having from 8 to 18 carbon atoms are preferred. These include, by way of illustration only, sodium caprylate (C6), sodium laurate (C10), sodium myristate (C12), sodium palmitate (C14), sodium oleate (C16, 1 double bond), and sodium stearate (C16). The alkali metal salt of a fatty acid is generally one which is solid at room temperature so that it forms a solid film on the skin in combination with the silicate. The fatty acid salt component comprises between 15 and 40 wt. %, especially between 20–30 wt. % of the surface coating composition.

An alkali-metal silicate is added to the composition in an amount effective to reduce the tackiness of the fatty acid component and to enhance the effectiveness of the topical barrier. The amount of alkali metal silicate added is between about 0.5 to 8 wt. %, preferably from about 0.5 to 3 wt. %. The alkali-metal silicate may be sodium silicate ($Na_4SiO_4$), potassium silicate, or may comprise a siloxane oligomer or polymer such as polydimethylsiloxane, or salt thereof, having equivalent characteristics.

The composition of the invention should have a viscosity suitable for topical application. A polyol may be added to achieve and maintain the proper viscosity, as well as to prevent excessive drying and cracking of the surface film. Polyols such as glycerin also act as emollients. Preferred polyols include glycerin, sorbitol and propylene glycol. The polyol is preferably used in an amount of 5 to 20 wt. % of the composition. The composition of the invention may further contain other additives such as pigments, emulsifiers, supplemental biocides, and the like.

The composition of the invention may be used in a variety of applications. One embodiment of the product is in response to the need for secondary topical barriers that will help protect health care workers (i.e., nurses, doctors, technicians), public servants (i.e., E.M.T.'s, police, fire personnel), home health care providers, family members, or anyone needing protection from infectious contact with another person's bodily fluids. Thousands of people, ordinarily through occupational choice, must face contact with such infectious fluids, some of which carry fatal infections (i.e., the HIV or AIDS virus). The lethal quality of this infection has justifiably created significant concern and apprehension among all those involved in health care and has manifested itself in two ways. First, greater numbers of people are choosing not to pursue or continue careers that place them at risk. Fewer employees results in correspondingly poorer quality and quantity of health care and public service for both infected and non-infected persons. Second, the possibility of AIDS has created a perception that all those being treated have a potentially fatal infection unless proven otherwise.

For health care applications, the composition of the invention both coats the skin with a protective barrier that inhibits infection from entering the body through the skin, and kills infectious organisms/viruses before they enter the body. The composition also coats and seals wounds with a protective barrier so as to prevent infection. Use of the composition in accordance with the method of the invention should provide a means of reducing the overall risk of infection and promote a more secure, less apprehensive attitude towards both infected and non-infected persons in health care workers.

An unexpected quality of the preferred composition of the invention, the skin cream described above, is its propensity to coat small cuts, abrasions, or sores with a somewhat thicker layer of barrier, thus making the most accessible areas for infection the most protected. Bodily fluids of another coming in contact with the barrier tend to release the antimicrobial agent, e.g., nonylphenoxypolyethoxyethanol, allowing it to destroy infectious organisms such as HIV. The skin film/coating allows the health care worker to apply a secondary barrier to skin, particularly in areas of the body which cannot be gloved or clothed, such as the face. This coating further provides a secondary barrier when applied to areas of the body where clothing or gowns or gloves suffer failure or saturation, such as the chest, abdomen, upper arms, face and hands, the outcome being a less infectious health care environment.

In light of the foregoing, a method of protecting a person working in proximity to bodily fluids such as blood or urine from infection from such fluids includes the initial step of applying to the skin of such a worker a protective composition consisting essentially of an aqueous base composition as described above and the antimicrobial agent. The base composition dries in a short time to form a film on the skin effective as a topical barrier against bodily fluids, i.e., that substantially prevents the contaminating fluids from reaching the skin. In addition, the film contains the antimicrobial agent in an amount effective to kill one or more types of infectious organisms, and can be removed with soap and water.

The health care worker wears the film while performing a task such as a surgical operation or medical procedure in close proximity to a patient which may be the source of infected bodily fluids, particularly HIV infected blood. Some surgical operations or procedures, such as open heart surgery, routinely involve contact between the blood of the patient and the physician. Incidental contact between the doctor and the patient's blood is nearly unavoidable in such situations, and in this context the method of the invention is particularly valuable.

The surgeon, nurse, technician or other medical worker normally puts on protective garments such as scrub suit, surgical gloves, mask and the like. Such garments can be worn over skin to which the protective composition has been applied to provide additional protection. The protective composition may also be applied to areas of skin which are not covered by protective garments, such as the face and neck.

The protective film is removed from the worker's skin upon completion of the task. For this purpose, the film of the invention must be readily removable, preferably by washing it from the skin with soap and water, to remove any residual contamination. For this purpose, the protective composition is preferably the cream discussed above consisting essentially of 15 to 40 wt. % of the alkali-metal fatty acid salt having from 8 to 18 carbon atoms, an effective amount of the antimicrobial compound, 5 to 20 wt. % of a polyol effective as an emollient, 0.5 to 8.0 wt. %, of an alkali metal silicate, and the balance water. However, other compositions comprising a removable film-forming base and an antimicrobial agent can be used.

After the medical operation, procedure, or other comparable task is done and the film has been removed, the method of the invention can be repeated during the same day, or even immediately. This permits the health care worker to perform one or more additional medical operations or procedures without risk of contaminating one patient with infection from another due to residual film on the skin. Antimicrobial skin compositions according to the prior designed for long term use are generally not suitable for this purpose.

Other uses for the composition of the invention also exist. The base composition, without the antimicrobial component, can be used in industry to protect portions of surface areas from finishing processes or unwanted dyes, inks or paints. Surfaces adjacent to those which are to be finished could be coated with the surface coating composition to form a temporary barrier from the finishing substance. This protective barrier could easily be removed with water after the finishing process was completed. The base composition can also be applied to metal surfaces, such as silver, to protect such surfaces from tarnishing.

It will be understood that the foregoing description is of preferred exemplary embodiments of the invention, and that the invention is not limited to the specific forms shown. Modifications may be made in the design and arrangement of the elements without departing from the scope of the invention as expressed in the appended claims.

The following example illustrates the invention:

EXAMPLE

A antimicrobial cream having the following composition of ingredients was prepared:

| | |
|---|---|
| Nonoxynol-9 | 4 wt. % |
| Sodium laurate | 25 wt. % |
| Sodium silicate | 1 wt. % |
| Glycerin | 14 wt. % |
| Purified water | Balance |

These ingredients are heated to approximately 70° C., then stirred until cool. The resulting cream is then stored in a tube or other conventional container for later use.

The foregoing composition was applied to a small open wound and observed to collect there, effectively filling in the wound. This additional protection for open wounds or sores, in combination with the low toxicity of the cream, is particularly effective for purposes of the invention.

We claim:

1. A protective skin cream composition consisting essentially of:
   (i) 15 to 40 wt. % of an alkali-metal fatty acid salt having from 8 to 18 carbon atoms,
   (ii) an effective amount an antimicrobial compound,
   (iii) 5 to 20 wt. % of a polyol effective as an emollient,
   (iv) 0.5 to 8.0 wt. % of an alkali metal silicate, and
   (v) the balance water, said composition being removable with soap and water.

2. The composition of claim 1, wherein the cream is in the form of an oil-in-water emulsion.

3. The composition of claim 1, wherein the polyol is selected from glycerin, sorbitol and propylene glycol, and the alkali metal silicate is sodium or potassium silicate.

4. The composition of claim 1, wherein the antimicrobial compound is selected from the group consisting of carboxylate, organopolysiloxane, nonoxynol-9, AZT, chlorhexidene, iodine, sodiumoxychlorosene, tetrachlorosalicylanilide, silver sulfadiazine, butaconazole nitrate, chloroxylenol, triacetin, and aluminum chlorhydrate.

5. The composition of claim 4, wherein the antimicrobial compound is AZT or nonylphenoxypolyethoxyethanol.

6. The composition of claim 1, wherein the antimicrobial compound is selected from the group consisting of chlorhexidene, iodine, sodium oxychlorosene, tetrachlorosalicylanilide, silver sulfadiazine, butaconazole nitrate, chloroxylenol, and fungicidal agents.

7. The composition of claim 1, wherein the antimicrobial compound is present in the amount of 0.1 to 15 wt. %.

8. The composition of claim 1, wherein the alkalimetal fatty acid salt is selected from the group consisting of sodium caprylate, sodium laurate, sodium myristate, sodium palmitate, sodium oleate, and sodium stearate.

9. The composition of claim 1, wherein the alkali metal silicate is sodium silicate, potassium silicate, or a siloxane oligomer or polymer or salt thereof.

10. A method of protecting a person from infection from bodily fluids, which comprises:
(1) applying to the skin of said person a protective skin cream composition of claim 1, which composition dries to form a film on the skin effective as a topical barrier against bodily fluids, the film containing the antimicrobial agent in an amount effective to kill one or more types of microbial organisms, and the film being removable with soap and water;
(2) wearing the film while performing a task in close proximity to said bodily fluids; and
(3) removing the film from said person's skin upon completion of a task with soap and water.

11. The method of claim 10, wherein the task comprises a surgical operation or procedure performed on a patient having blood.

12. The method of claim 11, wherein the surgical operation or procedure involves contact between the blood of the patient and a worker involved with said surgical operation or procedure.

13. The method of claim 11, further comprising a step of putting on a protective garment over skin to which the protective composition has been applied.

14. The method of claim 11, further comprising the steps of putting on protective garments, and applying the protective composition to exposed areas of skin.

15. The method of claim 12, further comprising applying the protective composition to said worker's face.

16. The method of claim 10, further comprising performing steps (1) to (3) two or more times during the same day.

* * * * *